US00PP09561P

United States Patent [19]

Poulsen

[11] Patent Number: Plant 9,561

[45] Date of Patent: May 21, 1996

[54] ELATIOR BEGONIA PLANT NAMED LEA

[76] Inventor: Jens N. Poulsen, Gartneriet J.N.P., Larsmindevej 1, Lisbjerg, DK-8200 Aarhus N., Denmark

[21] Appl. No.: 388,581

[22] Filed: Feb. 9, 1995

[51] Int. Cl.[6] ..... A01H 5/00

[52] U.S. Cl. ..... Plt./87.18

[58] Field of Search ..... Plt./87.18

*Primary Examiner*—James R. Feyrer

*Attorney, Agent, or Firm*—Proprietary Rights Intl.

[57] ABSTRACT

A distinctive cultivar of Elatior Begonia plant named Lea, characterized by its upright and spreading growth habit; compact plant size; freely branching habit; strong stems and stem base; small leaves; medium pink flower color; large number of flowers per raceme; small flowers; early and even flowering; strong and vigorous root system; and good post-production longevity.

1 Drawing Sheet

The present invention relates to a new and distinctive cultivar of Begonia plant, botanically known as *Begonia× hiemalis,* commercially known as Elatior Begonia, and referred to by the cultivar name Lea.

The new cultivar was discovered by the inventor in Aarhus, Denmark, as a mutation of the nonpatented Elatior Begonia cultivar Rikkie, and was obeserved in a group of 15-cm flowering plants of the parent.

Asexual reproduction of the new cultivar by tip cuttings in Aarhus, Denmark, has shown that the unique features of this new Elatior Begonia are stabilized and are reproduced true to type in successive propagations.

The new cultivar has not been observed under all possible environmental conditions. The phenotype may vary significantly with variations in environment such as temperature, light level and daylength, without, however, any variance in genotype.

The following traits have been repeatedly observed and are determined to be the unique characteristics of Lea. The following characteristics differentiate the new cultivar from the parent cultivar Rikke and other Elatior Begonias commercially know and used in the floriculture industry, namely the nonpatented cultivar Nelly:

1. Plants of the cultivar Lea are upright and spreading in growth habit. Plants of the cultivar Rikke are similar in plant habit to plants of Lea. Plants of the cultivar Nelly are more spreading compaed to plants of Lea.

2. Plants of the cultivar Lea are compact. Plants of the cultivar Lea are less vigorous and shorter than plants of the cultivars Rikke and Nelly.

3. Plants of the cultivar Lea do not require pinching to produce full plants as they are freely branching. Plants of the cultivar Rikke are similar in branching habit to plants of Lea. Plants of the cultivar Nelly are less freely branching compared to plants of Lea.

4. Plants of the cultivar Lea have strong stems and stem bases. Plants of the cultivars Lea, Rikke and Nelly are similar in stem strength. Plants of the cultivar Lea have greater stem base strength than plants of Rikke and Nelly.

5. Plants of the cultivar Lea have small leaves. Plants of the cultivar Rikke have leaves similar in size to plants of Lea. Leaves of plants of Nelly are larger than leaves of plants of Lea.

6. Flowers of the cultivar Lea are medium pink in color (Red Group 50C). In comparison, flowers of the cultivar Rikke are light orange in color (Yellow-Orange Group 23B), and flowers of the cultivar Nelly are light pink in color (Red Group 36B).

7. Plants of thc cultivar Lea have a large number of flowers per raceme. Plants of the cultivar Lea have more flowers per raceme than plants of Nelly and generally the same number of flowers per raceme as plants of Rikke.

8. Flowers of the cultivar Lea are small in diameter. Plants of the cultivar Lea have smaller flowers than plants of the cultivars Rikke and Nelly.

9. Plants of the cultivar Lea flower early. Plants of the cultivar Lea flower earlier than plants of the cultivars Rikke and Nelly.

10. Plants of the cultivar Lea are evenly covered with flowers. Plants of the cultivar Lea are more evenly covered with flowers than plants of the cultivars Rikke and Nelly.

11. Plants of the cultivar Lea have strong and vigorous root systems. Plants of the cultivar Lea have stronger and more vigorous root systems than plants of the cultivars Rikke and Nelly.

12. Plants of the cultivar Lea have good postproduction longevity. Plants of the cultivar Lea last longer in the interior environment than plants of the cultivars Rikke and Nelly.

The accompanying colored photograph illustrates the overall appearance and flower color of the new cultivar, showing the colors as true as it is reasonably possible to obtain in colored reproductions of this type. The photograph comprises a side perspective view of a typical potted plant of Lea.

The following observations, measurements, values, and comparisons describe plants grown in Aarhus, Denmark, under commercial practice in a glass-covered greenhouse with day and night temperatures ranging from 19 to 21C. Depending on cloud cover, light levels ranged from 5,000 to 35,000 lux.

In the following description, color references are made to The Royal Horticultural Society Colour Chart except where general terms of ordinary dictionary significance are used.

Botanical classification: *Begonia×hiemalis* cultivar Lea.

Commercial classificattion: Elatior Begonia.

Parentage: Naturally-occurring mutation of *Begonia×hiemalis* cultivar Rikke.

Propagation:

A. *Type.*—By tip cuttings.

B. *Time to initiate roots.*—Tip cuttings root in 17 to 20 days at temperatures of 21C.

C. *Rooting habit.*—Root system is very strong and develops rapidly. Roots are prolific and dense. Roots are fine and fibrous in texture.

Plant description:

A. *Plant form.*—Upright and spreading potted plant, freely branching with good stem and stem base strength. Flowers are fully double and abundant. Plants flower continuously under warm (higher than 18C) night temperatures.

B. *Growth habit.*—Moderate growth rate and vigor. Compact in plant habit with short internodes. Suitable for 10 to 15-cm containers. Under optimal environmental conditions, 10 to 12 weeks are required to produce proportional 12.5-cm potted plants (approximately 20 cm in height) from tip cuttings that are directly-stuck in the container. Vegetative shoots are formed at basal nodes and flowering shoots are formed at upper nodes.

C. *Foliage and stem description.*—1. Leaf arrangement: Simple, alternate. 2. Quantity of leaves: 20 to 30 per 12.5-cm potted plant. 3. Leaf length: 7 to 8 cm. 4. Leaf width: 9 to 10 cm. 5. Leaf shape: Cordate. 6. Leaf tip: Acute. 7. Leaf base: Obtuse. 8. Leaf margin: Serrate. 9. Leaf texture: a. Upper side: Smooth, leathery, glabrous. b. Under side: Leathery, sparsely pubescent. 10. Leaf color: a. Young foliage, upper side: 137A. b. Young foliage, under side: 138B. c. Mature foliage, upper side: 139A. d. Mature foliage, under side: 139C. 11. Leaf attachment: Stalked. 12. Petiole length: 1 to 1.2 cm. 13. Petiole diameter: 4 to 5 mm. 14. Petiole color: 139C. 15. Venation pattern: Palmate, smooth on upper side, raised on under side. 16. Venation color: a. Upper side: 141B. b. Under side: 139D. 17. Stem color: 139C. 18. Stem strength: Very strong. 19. Stem base strength: Very strong.

Flowering description:

A. *Flowering habit.*—Flowers arranged in racemes. Many racemes in flower simultaneously. Flowering continuous under warm (higher than 18C) night temperatures.

B. *Natural flowering season.*—Plants will flower year around regardless of daylength, however plants will flower earlier and more abundantly if daylength is 12 hours or less.

C. *Quantity of flowers.*—Six to 10 flowers per raceme, up to 50 flowers at various stages of development may be present per 12.5-cm pot.

D. *Flowers.*—1. Shape: Circular. 2. Diameter: 2.5 to 4 cm. 3. Height: 1.2 to 1.4 cm.

E. *Peduncle.*—1. Length: 0.5 to 1.2 cm. 2. Diameter: 2.5 mm. 3. Color: 147C. 4. Aspect: Erect. 5. Texture: Glabrous.

F. *Flower bud.*—1. Shape: Ovoid. 2. Diameter: 0.5 cm. 3. Length: 0.5 cm. 4. Rate of opening: 3 to 5 days. 5. Color: 49C.

G. *Tepals.*—1. Arrangement: Rosette. 2. Shape: Flat, rounded. 3. Quantity per flower: 8 to 20. 4. Length: 1 to 2.5cm. 5. Width: 1 to 2.5 cm. 6. Color: a. When opening: 49B. b. Fully open: (1) Upper side: 50C. (2) Under side: 49B. c. Fading to: 49B. 7. Margin: Entire. 8. Texture: Smooth, velvety, glabrous.

H. *Sepals.*—1. Arrangement: Opposite. 2. Shape: Oval. 3. Quantity per flower: 2. 4. Length: 1.5 cm. 5. Width: 1.3 cm. 6. Color: a. Upper side: 147B. b. Under side: 146D. 7. Tip: rounded, slightly pointed. 8. Margin: Entire. 9. Texture: Thin, transparent.

I. *Reproductive organs.*—1. Stamens: None. 2. Pistils: None.

Postproduction longevity:

A. *Individual flowers.*—Generally 2 to 3 weeks.

B. *Whole plants.*—Generally more than 6 weeks under interior conditions.

Disease resistance: Plants of the cultivar Lea are resistant to powdery mildew.

I claim:

1. A new and distinct Elatior Begonia plant named Lea, as illustrated and described.

* * * * *

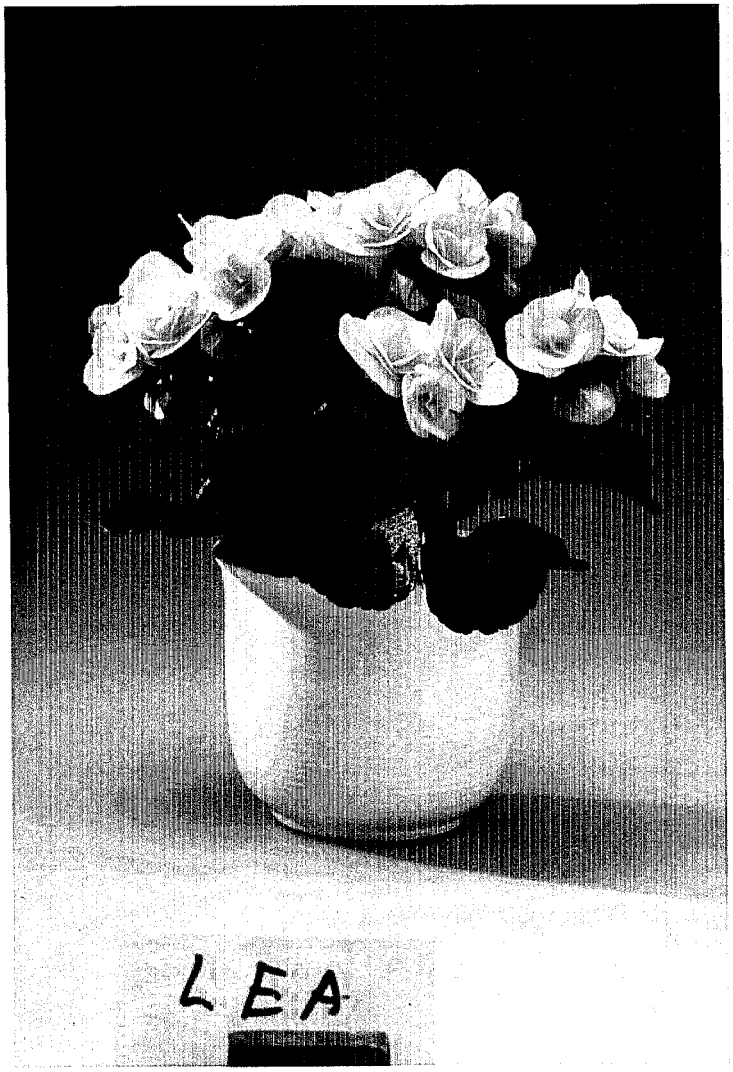
LEA